United States Patent [19]

Ohshima

[11] Patent Number: 4,489,712
[45] Date of Patent: Dec. 25, 1984

[54] ENDOSCOPE WITH A GAS/LIQUID SWITCHING MECHANISM

[75] Inventor: Yutaka Ohshima, Tokyo, Japan

[73] Assignee: Olympus Optical Co., Ltd., Tokyo, Japan

[21] Appl. No.: 440,579

[22] Filed: Nov. 10, 1982

[30] Foreign Application Priority Data

Nov. 20, 1981 [JP] Japan .................... 56-186246

[51] Int. Cl.³ .............................................. A61B 1/06
[52] U.S. Cl. .................................. 128/6; 137/625.48
[58] Field of Search ........................................ 128/4–8;
137/625.12, 625.13, 625.16, 625.48, 637.2,
637.5, 881, 882, 883, 597

[56] References Cited

U.S. PATENT DOCUMENTS

| 1,821,719 | 9/1931 | Messier | 137/625.48 |
| 3,297,046 | 1/1967 | Hall | 132/597 |
| 3,958,566 | 5/1976 | Furihata | 128/4 |
| 4,185,663 | 1/1980 | Stripting | 137/882 |
| 4,261,343 | 4/1981 | Ouchi et al. | 128/4 |
| 4,281,646 | 8/1981 | Kinoshita | 128/6 |
| 4,311,134 | 1/1982 | Mitsui et al. | 128/6 |

Primary Examiner—Edward M. Coven
Assistant Examiner—Max F. Hindenburg
Attorney, Agent, or Firm—Frishauf, Holtz, Goodman and Woodward

[57] ABSTRACT

An endoscope includes a connector portion attached to a universed cord of the endoscope, a gas feed tube and a liquid feed tube each connected at one end to a liquid feed tank, and an insertion member provided at the other ends of the gas feed tube and the liquid feed tube and capable of being attached to and detached from the connector portion. A movable member is provided at the connector portion and is capable of taking a first position in which a gas feed passage and a liquid feed passage of the endoscope communicate with the gas feed tube and the liquid feed tube, respectively, when the connector portion is connected to the insertion member, and a second position in which the gas feed passage and the liquid feed passage are disconnected from the gas feed tube and the liquid feed tube, respectively, and the liquid feed passage communicates with an air pump, when the insertion member is removed from the connector portion. Accordingly the interior of the liquid feed tank is pressurized by the air pump and a liquid in the tank is fed into the liquid feed passage through the liquid feed tube when the connector portion and the insertion member are connected, and gas is fed from the air pump directly into the liquid feed passage to discharge residual liquid when the insertion member is removed from the connector portion.

12 Claims, 6 Drawing Figures

F I G. 2
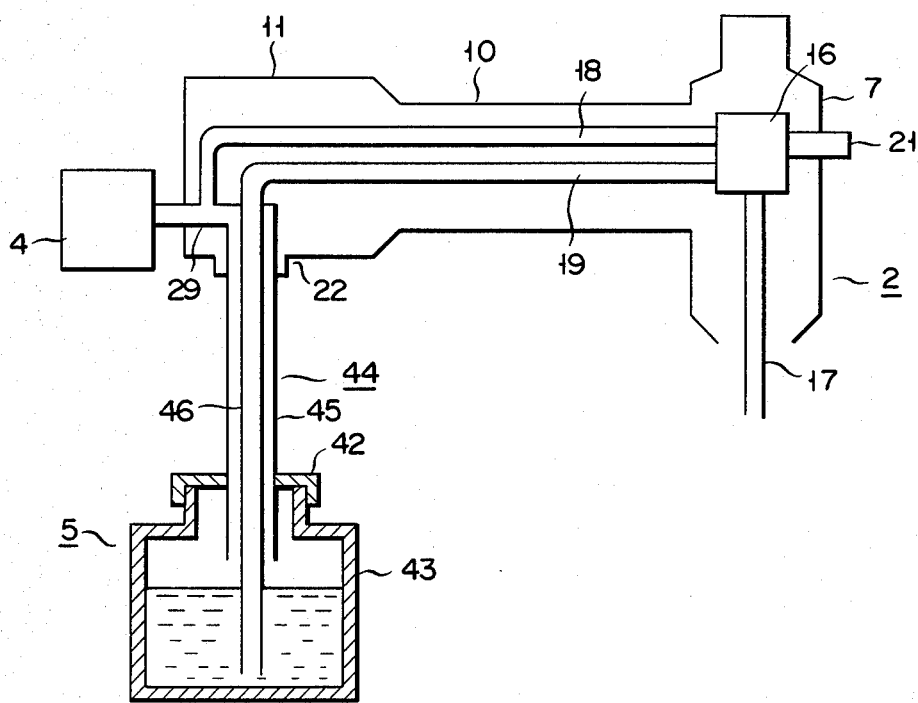

ENDOSCOPE WITH A GAS/LIQUID SWITCHING MECHANISM

BACKGROUND OF THE INVENTION

This invention relates to an endoscope in which a gas feed passage, and a liquid feed passage to carry gas and liquid, are formed in a main body.

In some endoscopes, a liquid feed passage is formed internally, a liquid inlet of the liquid feed passage is formed in a connector attached to a forward end of a universal cord, and a liquid outlet is formed in the distal end portion of the endoscope. Supplied through the liquid feed passage, a medical fluid may be sprayed in a body cavity, or water may be used to clean the outer surface of an objective lens. When using the endoscopes of this type for liquid feeding operation, the liquid would remain in the liquid feed passage after use if the use of the endoscope is suspended under a liquid feeding condition. In this case, if the liquid remaining in the liquid feed passage is left as it is, it could spoil or become contaminated by germs, etc. Thus, if the endoscope is used again with the liquid still remaining in the liquid feed passage, B-type hepatitis or hospital infection may be caused.

Accordingly, there has been proposed an improved endoscope as stated in Japanese Patent Disclosure No. 166794/79. In this endoscope, an air feed passage and a water feed passage are formed internally, and an air/water feed selector valve mechanism is provided so that the air or water feeding operation may be selected by switching an air/water selector valve. Also, an operating valve mechanism is used to feed compressed air into the water feed passage, thereby removing water from the water feed passage. In the endoscope of this construction, however, both the air/water feed selector valve mechanism and the operating valve mechanism require a manual valve switching operation by an operator. Thus, the operation is complicated and troublesome, and it is hard to judge whether the valves are in a water feeding state or whether they are in a draining state. Such a situation could easily lead to incorrect operation and would be hazardous.

SUMMARY OF THE INVENTION

An object of this invention is to provide an endoscope capable of readily and securely discharging water, a medical fluid, or some other liquid remaining in a liquid feed passage after the completion of a liquid feeding operation, as well as of reducing the possibility of incorrect operation in order to improve safety performance.

BRIEF DESCRIPTION OF THE DRAWINGS

FIGS. 1 to 4 show an endoscope according to one embodiment of this invention, in which FIG. 1 is a general perspective view showing an operating state, FIG. 2 is a schematic view showing the connection between a gas feed pump and a liquid feed pump for purposes of illustrating a liquid feeding operation, FIG. 3 is a sectional view of a connected portion, and FIG. 4 is a sectional view showing a connecting portion and the connected portions connected to each other; FIG. 5 is a sectional view of a connected portion, and FIG. 6 is a sectional view showing a connecting portion and the connected portions connected to each other.

DETAILED DESCRIPTION OF THE PREFERRED EMBODIMENTS

Figure 1:
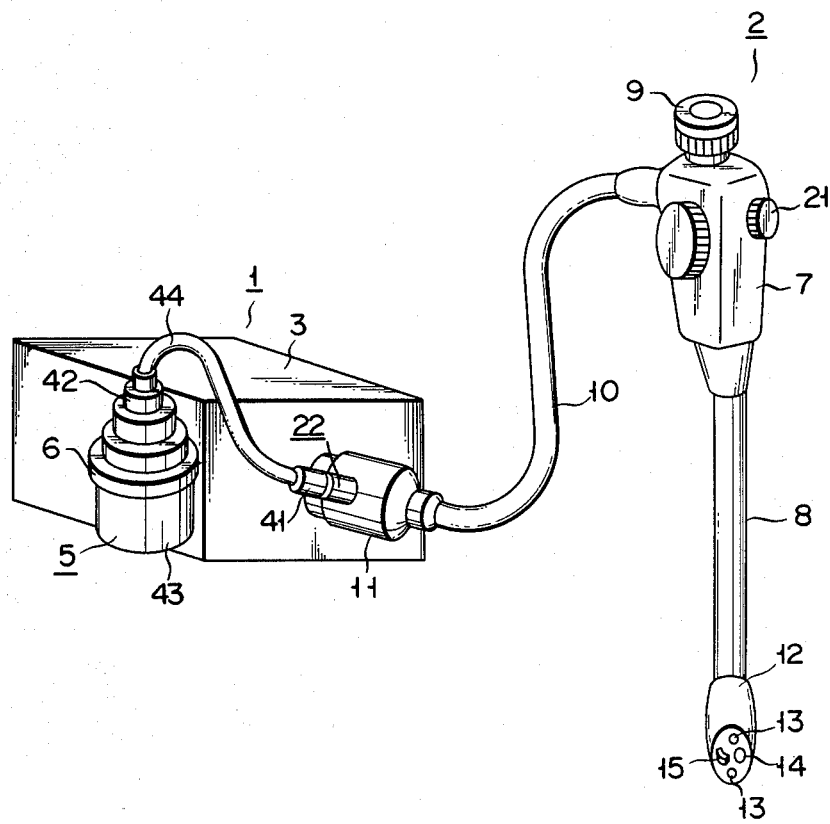
Figure 3:
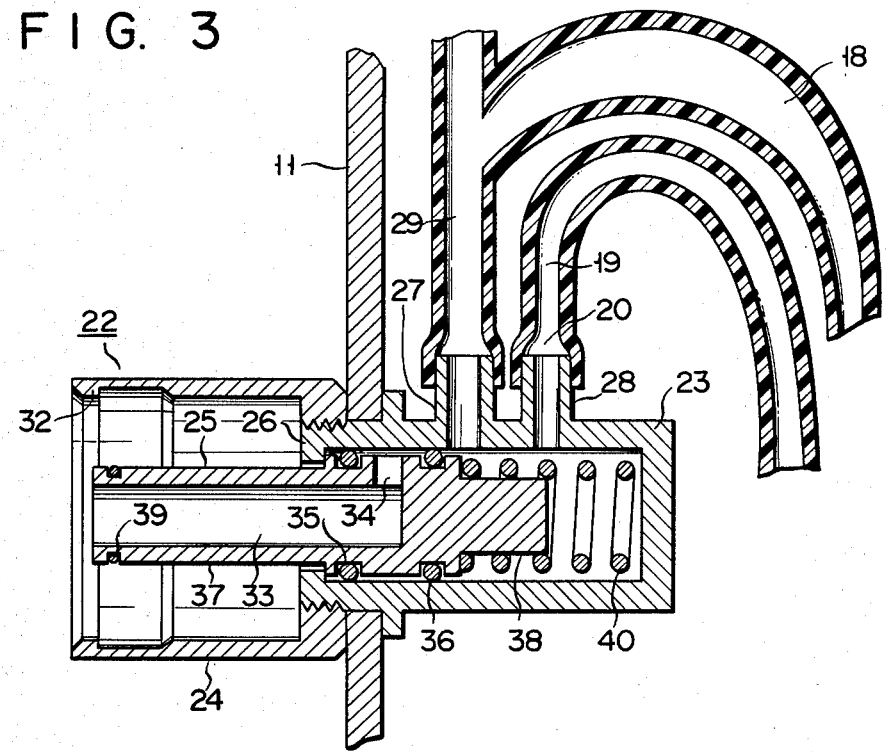

FIG. 1 shows an endoscope 2 connected to a gas/liquid feeding apparatus housing 1. The gas/liquid feeding apparatus housing 1 is integral with, for example, a light source unit. A gas feed pump 4 or gas feeding means (FIG. 2), a light source lamp (not shown), etc., are disposed in a casing 3 of the apparatus housing 1, and a liquid feed tank 5 is removably attached to a side plate of the casing 3 by means of a fixing ring 6. The main body of the endoscope 2 is formed of an operating section 7 and an insertion section 8. The operating section 7 is provided with an eyepiece section 9, and is connected with a universal cord 10. The distal end of the universal cord 10 is fitted with a connector 11 which is removably connected to the gas/liquid feeding apparatus housing 1. A distal end portion 12 is provided at the distal end of the insertion section 8. The distal end portion 12 is provided with illumination windows 13 connected to an illumination optical system, an objective lens 14 connected to an observation optical system, and a discharge port 15 through which gas or liquid is discharged. As shown in FIG. 2, moreover, a selector valve 16 is disposed inside the operating section 7 of the main body of the endoscope 2. The selector valve 16 is connected to the discharge port 15 by means of a gas/liquid feed passage 17 formed of a synthetic resin tube. A gas feed passage 18 and a liquid feed passage 19 each formed of a synthetic resin tube are arranged in the universal cord 10. The respective one end portions of the gas feed passage 18 and the liquid feed passage 19 are coupled to the selector valve 16. The other end portion of the gas feed passage 18 is connected to a connection port in the distal end face of the connector 11 so that the gas feed passage 18 is connected to the gas feed pump 4 through the connection port when the connector 11 is connected to the gas/liquid feeding apparatus housing 1. The other end portion of the liquid feed passage 19 communicates with a liquid inlet port 20 in the connector 11. Thus, the air feed passage 18 or the liquid feed passage 19 may be caused to selectively communicate with the gas/liquid feed passage 17 by the selector valve 16. The selector valve 16 makes a selection between gas and liquid feeding operations when an operating button 21 at the operating section 7 is pushed externally. A connected portion 22 is formed on the lateral surface of the connector 11. The connected portion 22 constitutes a switching mechanism, and is formed of a cylinder member 23 set in the connector 11 with its screw portion projected outward from the connector 11, a connecting member 24 in the form of a cylinder open at both ends and coaxially screwed on the screw portion of the cylinder member 23 at the rear end opening side, and a cylindrical movable member 25 slidable in the cylinder member 23. The cylinder member 23 is in the form of a bottomed cylinder which has the screw portion on the outer peripheral surface near its open end portion and a projected portion 26 protruding inward from its inner peripheral surface. Inside the connector 11, first and second connection ports 27 and 28 protrude outward from the outer peripheral surface of the cylinder member 23. The connection ports 27 and 28 have their respective communication holes opening into the cylinder member 23. The first connection port 27 is connected with a forked gas feed passage (communicating means) 29 communicating with the gas feed passage 18, while the second connection port 28 is connected with the liquid inlet port 20 of the liquid feed passage 19. From the inner peripheral surface of the connecting member 24 at the front end opening portion thereof protrudes a ring-shaped retaining portion 32 which retains a C-ring (FIG. 4) of an insertion member (connecting portion) 30 mentioned later. A circular bore portion 33 extending to the rear end side is formed in the center of the front end face of the movable member 25. In the outer peripheral surface of the movable member 25 a communication hole 34 is formed, opening into the bore portion 33. O-rings 35 and 36 are fitted on those portions of the outer peripheral surface of the thick middle portion of the movable member 25 which lie before and behind the communication hole 34, respectively. The O-rings 35 and 36 prevent liquid from leaking into the communication hole 34. Narrow portions 37 and 38 are formed in front of the O-ring 35 and at the back of the O-ring 36, respectively. The outside diameter of the front narrow portion 37 is substantially smaller than the inside diameter of the projected portion 26 of the cylinder member 23 so that an annular gap is formed between the narrow portion 37 and the projected portion 26. An O-ring 39 is fitted on the outer peripheral surface of the narrow portion 37 at its front end portion. The rear narrow portion 38 is fitted with one end of a compression coil spring 40 in the cylinder member 23. The movable member 25 is urged forward by the urging force of the coil spring 40, and is normally held in a projected position or forward position where the thick middle portion is caught by the projected portion 26, as shown in FIG. 3. In this position, the liquid feed passage 19 is connected to the forked gas feed passage 29 through the second connection port 28, a space between the cylinder member 23 and the rear narrow portion 38 of the movable member 25, and the first connection port 27. In this position, moreover, the movable member 25 moves as a mouthpiece 41 (mentioned later) is attached or detached.

Figure 4:
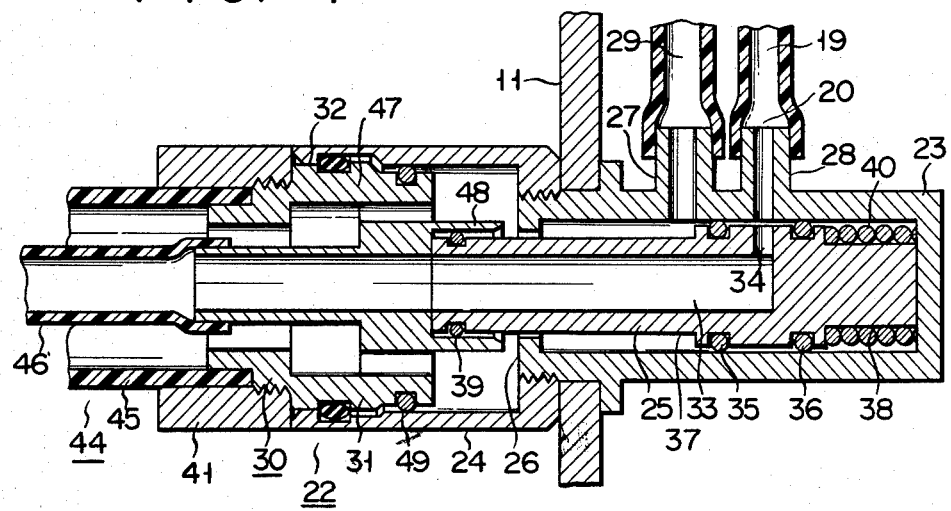

The liquid feed tank 5, whose top opening portion is closed by a cover 42, is composed of a closed container 43 containing therein a liquid such as water or a medical fluid. The cover 42 is fitted with the proximal end portion of a coupling tube 44. The coupling tube 44 has a double-tube structure, consisting of a thick gas feed tube 45 and a narrow liquid feed tube 46 therein. As shown in FIG. 2, the respective proximal end portions of the air feed tube 45 and the liquid feed tube 46 penetrate the cover 42 to be inserted into the closed container 43. The open ends of the gas feed tube 45 and the liquid feed tube 46 are held at the upper and lower portions, respectively, of the interior of the closed container 43. The aforementioned cylindrical mouthpiece 41 open at both ends is attached at one opening portion to the distal end portion of the coupling tube 44. As shown in FIG. 4, the insertion member 30 is coaxially screwed in the other opening portion of the mouthpiece 41. The insertion member 30 is integrally formed of a thick air feed mouthpiece 47 and a narrow liquid feed mouthpiece 48 coaxially disposed in the gas feed mouthpiece 47. A plurality of axially extending communication holes are formed between the air feed mouthpiece 47 and the liquid feed mouthpiece 48. The distal end portion of the gas feed tube 45 is attached to the front portion of the gas feed mouthpiece 47, while the distal end portion of the liquid feed tube 46 is attached to the front portion of the liquid feed mouthpiece 48. The C-ring 31 and an O-ring 49 are fitted on the outer peripheral surface of the gas feed mouthpiece 47. If the mouthpiece 41 is connected to the connected portion 22 of the connector 11, the movable member 25 is pushed in against the urging force of the coil spring 40 by a stepped portion formed on the inner peripheral surface of the liquid feed mouthpiece 48 at the rear portion thereof. When the movable member 25 moves to the depressed position where the C-ring 31 of the gas feed mouthpiece 47 is caught by the retaining portion 32 of the connecting member 24, the communication hole of the second connection port 28 aligns with the communication hole 34 of the movable member 25. At the same time, the liquid feed passage 19 is allowed to communicate with the liquid feed tube 46 by means of the second connection port 28, the communication hole 34, the bore portion 33, and the liquid feed mouthpiece 48. Also, the forked gas feed passage 29 is allowed to communicate with the gas feed tube 45 by means of the first connection port 27, an annular space between the front narrow portion 37 of the movable member 25 and the cylinder member 23, an annular gap between the front narrow portion 37 and the projected portion 26 of the cylinder member 23, the interior of the connecting member 24, and the gas feed mouthpiece 47.

In operation, in the arrangement described above, the connector 11 of the endoscope 2 is connected to the gas/liquid feeding apparatus housing 1, and the mouthpiece 41 of the coupling tube 44 is connected to the connected portion 22 of the connector 11, as shown in FIG. 1. When the connector 11 of the endoscope 2 is connected to the gas/liquid feeding apparatus housing 1, the gas feed passage 18 of the connector 11 is connected to the air feed pump 4. When the mouthpiece 41 is connected to the connected portion 22 of the connector 11, the liquid feed passage 19 and the forked gas feed passage 29 are connected to the liquid feed tube 46 and the gas feed tube 45, respectively, as shown in FIG. 4. In this state, therefore, if the operating button 21 is pushed in to switch the selector valve 16 thereby blocking the gas feed passage 18, compressed air supplied from the gas feed pump 4 is led from the gas feed passage 18 of the connector 11 into the forked gas feed passage 29, and is further fed into the closed container 43 of the liquid feed tank 5 through the gas feed tube 45 of the coupling tube 44. Accordingly, the internal pressure of the closed container 43 increases, so that the water, medical fluid or some other liquid in the closed container 43 is fed into the liquid feed passage 19 of the endoscope 2 through the liquid feed tube 46, and is further led into the gas/liquid feed passage 17 through the selector valve 16.

If the mouthpiece 41 of the coupling tube 44 is removed from the connector 11 of the endoscope 2 after the liquid feeding operation is completed, the movable member 25 is pushed back to the projected position shown in FIG. 3 by the urging force of the coil spring 40. Thus, the communication hole 34 of the movable member 25 is blocked by the cylinder wall of the cylinder member 23, and the water or medical fluid remaining in the liquid feed passage 19 and the gas/liquid feed passage 17 can be discharged to the outside through the discharge port 15 at the end of the liquid feeding operation.

Figure 5:
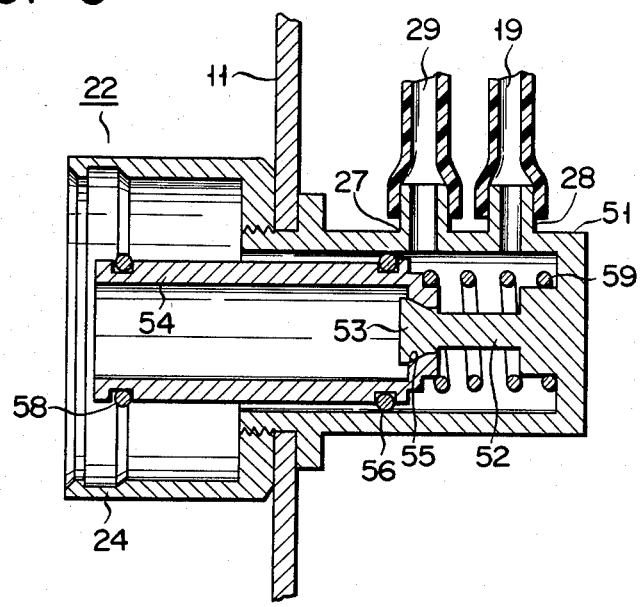
FIGS. 5 and 6 show an endoscope according to another embodiment of the invention.
Figure 6:
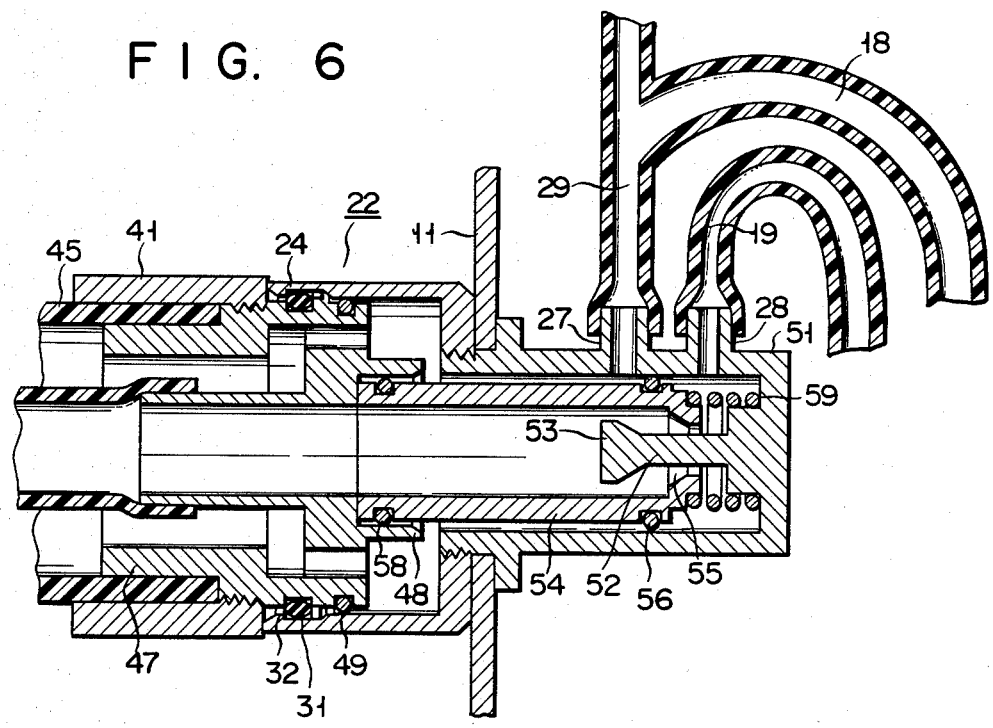

Referring now to FIGS. 5 and 6, another embodiment of the invention will be described. In this embodiment, a projected portion 52 coaxially protrudes from the bottom portion of a cylinder member 51 of a connected portion 22, constituting a switching mechanism, into the cylinder member 51. A valve plug 53 in the form of a truncated cone is formed at the extreme end of the projected portion 52. A valve seat 55 corresponding in shape to the valve plug 53 is formed at the bottom portion of a movable member 54 which is in the form of a bottomed cylinder axially movable within the cylinder member 51. The movable member 54 has such an outside diameter that an annular space is defined between its outer peripheral surface and the inner peripheral surface of the cylinder member 51. An O-ring 56 is fitted on the outer peripheral surface of the movable member 54 on the valve seal side so as to seal the annular space. Another O-ring 58 is fitted on the opening-side portion of the outer peripheral surface of the movable member 54. Also, a compression coil spring 59 is fitted in the cylinder member 51 on the valve seat side of the movable member 54. The movable member 54 is normally held by the urging force of the coil spring 59 in a projected position or forward position where the valve seat 55 is pressed against the valve plug 53 of the cylinder member 51 to close the valve, as shown in FIG. 5. In this state, a liquid feed passage 19 communicates with a forked gas feed passage 29 by means of a second connection port 28, a space inside the cylinder member 51, and a first connection port 27. If a mouthpiece 41 of a coupling tube 44 is connected to the connected portion 22 of a connector 11, the movable member 54 is pushed backward against the urging force of the coil spring 59 by a liquid feed mouthpiece 48. When the movable member 54 moves to a depressed position where a C-ring 31 of a gas feed mouthpiece 47 is caught by a retaining portion 32 of a connecting member 24, the valve seat 55 is separated from the valve plug 53 of the cylinder member 51. Thus, the liquid feed passage 19 is allowed to communicate with a liquid feed tube 46 by means of the inside space of the cylinder member 51, a gap between the valve seat 55 and the projected portion 52, the interior of the movable member 54, and the liquid feed mouthpiece 48, while the forked gas feed passage 29 is allowed to communicate with the gas feed tube 45 by means of the first connection port 27, the space between the outer peripheral surface of the movable member 54 and the inner peripheral surface of the cylinder member 51, the interior of the connecting member 24, and the gas feed mouthpiece 47.

As in the first embodiment, therefore, if the mouthpiece 41 of the coupling tube 44 is connected to the connected portion 22 of the connector 11, the liquid feed passage 19 is connected to the liquid feed tube 46, and the forked air feed passage 29 is connected to the gas feed tube 45. Thus, when the operating button 21 is pushed to switch the selector valve 16 in this state, compressed air supplied from the gas feed pump 4 is led into the closed container 43 of the liquid feed tank 5 to increase the internal pressure of the closed container 43. Then, a liquid such as water, a medical fluid, etc., in the closed container 43 can be fed into the liquid feed passage 19 of the endoscope 2 through the liquid feed tube 46, and further into the gas/liquid feed passage 17 through the selector valve 16.

If the mouthpiece 41 of the coupling tube 44 is removed from the connector 11 of the endoscope 2 after the liquid feeding operation is completed, the movable member 54 is pushed back to the projected position shown in FIG. 5 by the urging force of the coil spring 59. As a result, the valve seat 55 of the movable member 54 is pressed against the valve plug 53 of the cylinder member 51 to stop the space between the valve seat 55 and the valve plug 53, and the liquid feed passage 19 is connected to the forked gas feed passage 29. Also in this case, therefore, the compressed air supplied from the gas feed pump 4 can be led into the liquid feed passage 19 through the gas feed passage 18, the forked gas feed passage 29, and the interior of the cylinder member 51, and the water or medical fluid remaining in the liquid feed passage 19 and the gas/liquid feed passage 17 can be discharged to the outside through the discharge port 15 at the end of the liquid feeding operation.

This invention is not limited to the aforementioned embodiments. For example, the mechanism for connecting the mouthpiece 41 of the coupling tube 44 and the connected portion 22 of the connector 11 may be modified as required. It is to be understood, moreover, that various other changes and modifications may be effected by one skilled in the art without departing from the scope or spirit of the invention.

According to this invention, as described above, a switching mechanism, which operates as a liquid feed tube to lead out a liquid in a liquid feed tank, is connected or disconnected. If the liquid feed tube is connected, a liquid feed passage in an apparatus housing is allowed to communicate with the liquid feed tube of the liquid feed tank, and a gas feed passage in the apparatus housing is allowed to communicate with an air feed tube. If the liquid feed tube is disconnected, on the other hand, the liquid feed passage in the apparatus housing is connected to the gas feed tube. Thus, after the liquid feeding operation is completed, water, medical fluid or some other liquid remaining in the liquid feed passage can be securely discharged to the outside with ease. Since the switching operation of the switching mechanism is performed in conjunction with the attachment or detachment of the liquid feed tube, there is no possibility of incorrect operation, and safety performance is improved. Moreover, the liquid feed passage in the apparatus housing is cut off from the outside when the liquid feed tube is removed, so that there is no fear of any foreign substances entering the liquid feed passage.

What is claimed is:

1. An endoscope capable of gas and liquid feeding operations by the use of gas feeding means and a liquid feed tank, comprising:
   an endoscope body having a gas feed passage and a liquid feed passage;
   a connected portion attached to the endoscope body for enabling communication with the gas feed passage and the liquid feed passage of the endoscope body;
   a gas feed tube and a liquid feed tube each connected at one end to the liquid feed tank;
   a connecting portion provided at the other ends of the gas feed tube and the liquid feed tube and capable of being attached to and detached from the connected portion of the endoscope body;
   communicating means for interconnecting the gas feeding means and the gas feed passage in the endoscope body; and
   a switching mechanism provided at the connected portion and capable of taking a first position in which the gas feed passage and the liquid feed passage communicate with the gas feed tube and the liquid feed tube, respectively, when the connecting portion is connected to the connected portion, and a second position in which the gas feed passage and the liquid feed passage are disconnected from the gas feed tube and the liquid feed tube, respectively, and the liquid feed passage communicates with the gas feeding means through the communicating means when the connecting portion is removed from the connected portion, wherein the interior of the liquid feed tank is pressurized by the gas feeding means and a liquid in the tank is fed into the liquid feed passage through the liquid feed tube and the switching mechanism when the connected portion and the connecting portion are connected, and wherein gas is fed from the gas feeding means into the liquid passage through the switching mechanism when the connecting portion is removed from the connected portion;

wherein said switching mechanism includes a cylinder member fixed to the connected portion and open at one end, and a connecting cylinder coaxially fixed to the opening side of the cylinder member and open at both ends, a movable member which is axially movable in the cylinder member and the connecting cylinder, and urging means for urging the movable member toward the connecting cylinder, said movable member being moved in one direction by the urging means to take said second position, and pushed by the connecting portion to move in the other direction against the urging force of the urging means to take said first position when the connecting portion is connected to the connected portion.

2. The endoscope according to claim 1, wherein said movable member has an axially extending bore portion formed in one end face thereof located in the connecting cylinder and a communication hole formed in an outer peripheral surface portion located in the cylinder member and opening into the bore portion, and said cylinder member has a first connection port communicating with the gas feed passage and a second connection port communicating with the liquid feed passage, so that, when the connecting portion is inserted into the connecting cylinder to be connected thereto, the liquid feed passage communicates with the liquid feed tube by means of the second connection port, the communication hole, and the bore portion, and the gas feed passage communicates with the air feed tube by means of the first connection port, the cylinder member, and the connecting cylinder, and that, when the connecting cylinder is removed from the connecting portion, the movable member is moved toward the connecting cylinder by the urging means to cause the liquid feed passage to communicate with the gas feed passage by means of the second connection port, the cylinder member, and the first connection port.

3. The endoscope according to claim 2, wherein said connecting portion includes a liquid feed mouthpiece connected to the other end of the liquid feed tube and a gas feed mouthpiece connected to the other end of the gas feed tube, the liquid feed mouthpiece moving said movable member against the urging means.

4. The endoscope according to claim 3, wherein said liquid feed mouthpiece is disposed coaxially in the gas feed mouthpiece, said gas feed mouthpiece being arranged to be inserted coaxially into the connecting cylinder for engagement.

5. The endoscope according to claim 1, wherein said movable member has an axially extending bore portion formed in one end face thereof located in the connecting cylinder and a valve seat formed on the other end face located in the cylinder member and connected to the bore portion, and said cylinder member has a first connection port communicating with the gas feed passage, a second connection port communicating with the liquid feed passage, and a valve plug protruding axially from an internal closed end wall surface of the cylinder member to engage the valve seat, thereby closing the same when the movable member is moved toward the connecting cylinder by the urging means, and to be disengaged from the valve seat, thereby opening the valve seat, when the movable member is moved toward the cylinder member against the urging means, so that, when the valve seat is closed, the liquid feed passage communicates with the gas feed passage by means of the second connection port, the cylinder member, and the first connection port, and that, when the valve seat is opened, the liquid feed passage communicates with the liquid feed tube by means of the second connection port, the cylinder member, the valve seat, and the movable member, and the gas feed passage communicates with the gas feed tube by means of the first connection port and the cylinder member.

6. The endoscope according to claim 1, including a housing for containing the gas feeding means and means on the housing for allowing the liquid feed tank to be removably attachable to the housing, and wherein the connected portion of the endoscope body is mounted on the housing for communicating the gas feed passage of the endoscope body with the gas feeding means in the housing.

7. The endoscope according to claim 1, wherein said endoscope body includes a flexible universal cord for containing the gas feed passage and the liquid feed passage, and a main body connected to the universal cord, the main body comprising an operating section and an insertion section.

8. The endoscope according to claim 7, wherein said insertion section of the main body of the endoscope contains a gas/liquid feed passage for directing a selected one of gas and liquid to a discharge port at the distal end of said insertion section.

9. The endoscope according to claim 8, including a selector valve in said operating section of the main body for selectively communicating one of the gas feed passage and the liquid feed passage in said universal cord with said gas/liquid feed passage in said insertion section.

10. The endoscope according to claim 4, wherein said liquid feed mouthpiece and said gas feed mouthpiece are integrally formed.

11. The endoscope according to claim 4, including a C-ring fitted on the outer peripheral surface of said gas feed mouthpiece, said connecting cylinder of said switching mechanism including a ring-shaped retaining portion on its inner peripheral surface in the region of the open end of said connecting cylinder further from the opening side of the cylinder member of said switching mechanism, for retaining said C-ring when said gas feed mouthpiece is inserted into said connecting cylinder.

12. The endoscope according to claim 11, including an O-ring fitted on the outer peripheral surface of said gas feed mouthpiece for sealingly engaging the inner peripheral surface of said connecting cylinder.

* * * * *